(12) United States Patent
Zhang et al.

(10) Patent No.: US 12,071,444 B2
(45) Date of Patent: Aug. 27, 2024

(54) SYNTHESIS AND USE OF OXA-SPIRODIPHOSPHINE LIGAND

(71) Applicant: SHENZHEN CATALYS TECHNOLOGY CO., LTD, Shenzhen (CN)

(72) Inventors: Xumu Zhang, Shenzhen (CN); Genqiang Chen, Shenzhen (CN); Jiaming Huang, Shenzhen (CN)

(73) Assignee: SHENZHEN CATALYS TECHNOLOGY CO., LTD, Shenzhen (CN)

( * ) Notice: Subject to any disclaimer, the term of this patent is extended or adjusted under 35 U.S.C. 154(b) by 3 days.

(21) Appl. No.: 17/689,925

(22) Filed: Mar. 8, 2022

(65) Prior Publication Data

US 2022/0185835 A1   Jun. 16, 2022

Related U.S. Application Data

(63) Continuation of application No. 16/770,087, filed on Jun. 5, 2020, now Pat. No. 11,299,507.

(51) Int. Cl.
| | |
|---|---|
| C07F 15/00 | (2006.01) |
| B01J 31/22 | (2006.01) |
| B01J 31/24 | (2006.01) |
| C07C 51/36 | (2006.01) |
| C07F 9/6561 | (2006.01) |

(52) U.S. Cl.
CPC ....... *C07F 15/0046* (2013.01); *B01J 31/2213* (2013.01); *B01J 31/249* (2013.01); *C07C 51/36* (2013.01); *C07F 9/6561* (2013.01); *B01J 2231/645* (2013.01); *B01J 2531/821* (2013.01); *C07B 2200/07* (2013.01)

(58) Field of Classification Search
CPC ...................................................... B01J 31/249
See application file for complete search history.

(56) References Cited

U.S. PATENT DOCUMENTS

| | | | |
|---|---|---|---|
| 11,299,507 B2 * | 4/2022 | Zhang | C07F 15/0053 |
| 2021/0340168 A1 * | 11/2021 | Chen | C07F 15/0053 |

OTHER PUBLICATIONS

American Chemical Society Chemical Abstract Service. RN 2305757-36-0, entered into STN/first available to public on Apr. 29, 2019. (Year: 2019).*

* cited by examiner

*Primary Examiner* — John S Kenyon

(57) ABSTRACT

The present invention relates to the technical field of chiral synthesis, and specifically provides the synthesis and use of a new type of oxa-spirodiphosphine ligands. The bisphosphine ligand is prepared with oxa-spirobisphenol as a starting material after triflation, palladium catalyzed coupling with diaryl phosphine oxide, reduction of trichlorosilane, further palladium catalyzed coupling with diaryl phosphine oxide, and further reduction of trichlorosilane. The oxa-spiro compound has central chirality, and thus includes L-oxa-spirodiphosphine ligand and R-oxa-spirodiphosphine ligand. The racemic spirodiphosphine ligand is capable of being synthesized from racemic oxa-spirobisphenol as a raw material. The present invention can be used as a chiral ligand in the asymmetric hydrogenation of unsaturated carboxylic acids. The complex of the ligand with ruthenium can achieve an enantioselectivity of greater than 99% in the asymmetric hydrogenation of methyl-cinnamic acid.

6 Claims, 1 Drawing Sheet

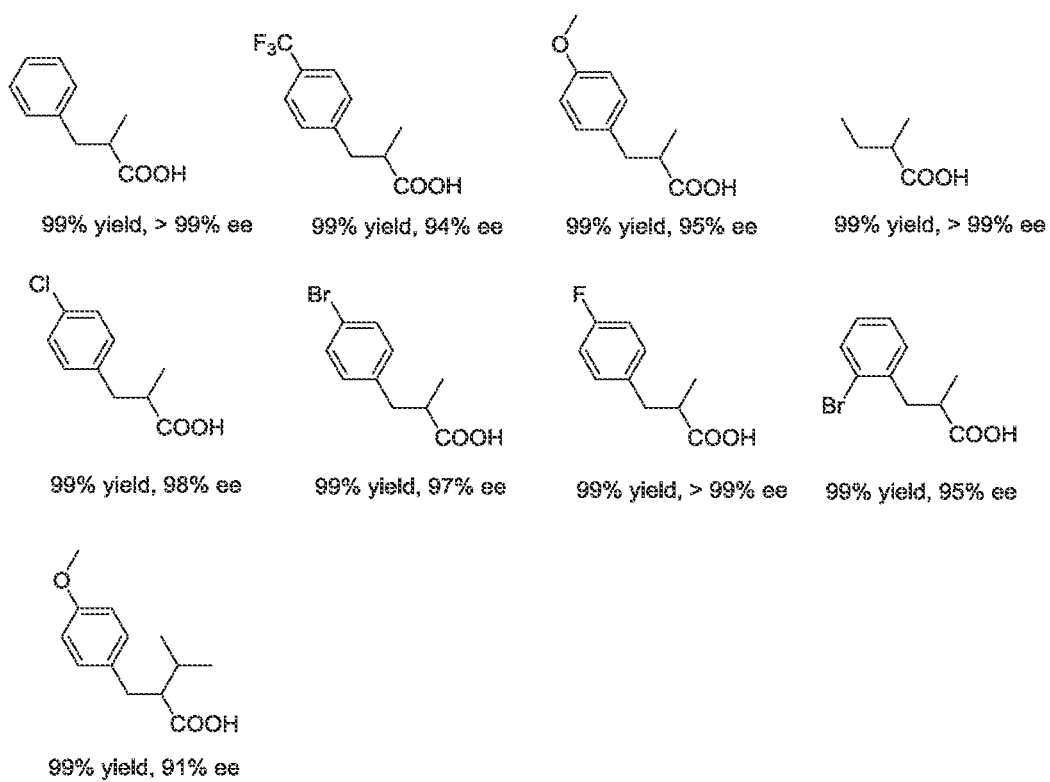

SYNTHESIS AND USE OF OXA-SPIRODIPHOSPHINE LIGAND

CROSS REFERENCE TO RELATED APPLICATION

The application is a continuation of and claims priority to U.S. patent application Ser. No. 16/770,087 filed on Jun. 5, 2020, which is a 371 of PCT application PCT/CN2018/075860 filed on Feb. 8, 2018, the disclosures thereof are herein incorporated by reference.

TECHNICAL FIELD

The present invention relates to the field of asymmetric catalysis, and particularly to the synthesis of a novel oxa-spirodiphosphine ligand. The compound can be used as a chiral ligand in asymmetric catalytic reactions and has high potential of use in the field of asymmetric catalysis.

BACKGROUND

In the past few decades, asymmetric catalysis has achieved rapid development. Various chiral ligands have been synthesized and used in the field of asymmetric catalysis. Among numerous chiral ligands, the diphosphine ligand is one of the ligands that are most widely used and extensively studied so far. It exhibits excellent activity and enantioselectivity in asymmetric hydrogenation, asymmetric hydroformylation, asymmetric Pauson-Khand reaction, asymmetric Heck reaction, asymmetric cycloaddition reaction, and asymmetric cycloisomerisation reaction, etc.

MOP synthesized by the Kagan's team, BINAP developed by the Noyori's team, and DIPAMP ligand developed by the Knowles' team are milestones in the development history of diphosphine ligands. They have been widely used in academia and industry. Then various chiral diphosphine ligands were synthesized, for example, SegePhos, Difluo-Phos, SynPhos, $C_n$-TunePhos, TangPhos, DuanPhos, Zhang-Phos, SKP, SDP, and SFDP.

Although chiral diphosphine ligands are now very rich in both types and numbers, each ligand has its unique properties. Therefore, the development of new chiral diphosphine ligands is of great importance.

SUMMARY

In view of the problems needed to be overcome in the prior art, the present invention provides an oxa-spirodiphosphine ligand having a structure of general Formula (I) below:

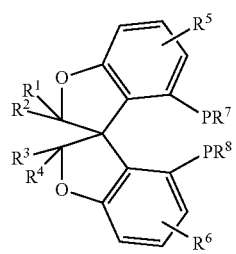

(I)

where in general Formula (I):

$R^1$ and $R^2$ are independently alkyl, alkoxy, aryl, aryloxy, or hydrogen, in which $R^1$, $R^2$, $R^3$ and $R^4$ may or may not form a ring; $R^5$ and $R^6$ are independently alkyl, aryl, or hydrogen; and $R^7$ and $R^8$ are alkyl, benzyl, or aryl.

The term alkyl is preferably methyl, ethyl, propyl, butyl, or the like.

The term alkoxy is preferably methoxy, ethoxy, propoxy, butoxy, or the like.

The aryl is preferably phenyl that is unsubstituted or substituted with alkyl or alkoxy as defined above.

The aryloxy is preferably methoxyphenyl, ethoxyphenyl or the like.

Further preferably, $R^1$, $R^2$, $R^3$, $R^4$, $R^5$, and $R^6$ are all hydrogen.

The oxa-spirodiphosphine ligand is the (±)-oxa-spirodiphosphine ligand, the (±)-oxa-spirodiphosphine ligand, or the (−)-oxa-spirodiphosphine ligand.

In a further preferred embodiment, the oxa-spirodiphosphine ligand is a compound having a structure below

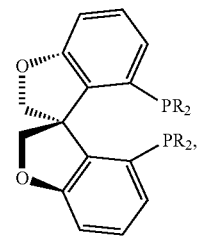

6 in which, preferably, Ar is alkyl, benzyl or aryl; and most preferably Ar is phenyl, or phenyl substituted with alkyl or alkoxy.

The alkyl and alkoxy are as defined above.

Another object of the present invention is to provide a method for synthesizing the compound by the following route:

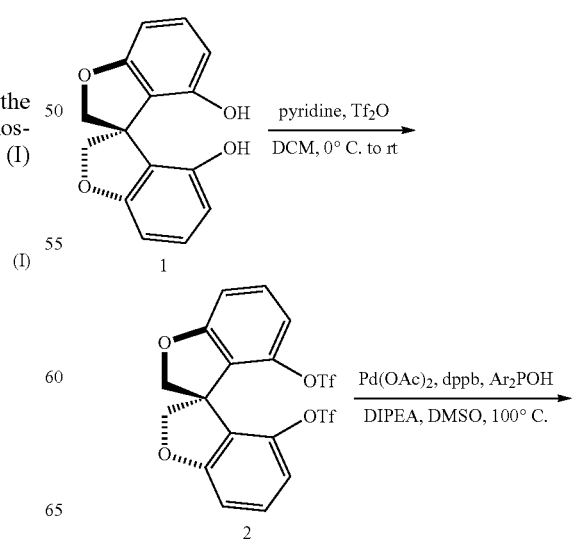

*-continued*

3

Structure 3: benzofuran-spiro compound with P(O)Ar₂ and OTf substituents
→ HSiCl₃, DIPEA / Toluene, 120° C.

4

Structure 4: benzofuran-spiro compound with PAr₂ and OTf substituents
→ Pd(OAc)₂, dppb, Ar₂POH / DIPEA, DMSO, 100° C.

5

Structure 5: benzofuran-spiro compound with PAr₂ and P(O)Ar₂ substituents
→ HSiCl₃, DIPEA / Toluene, 120° C.

6

Structure 6: benzofuran-spiro bisphosphine compound with two PAr₂ groups

Another object of the present invention is to provide use of the compound in catalyzing asymmetric reactions including hydrogenation reaction, hydroformylation reaction, hydrosilation reaction, hydroboration reaction, hydroxylation with hydrogen peroxide, hydroamination reaction, hydrocyanation reaction, isomerization and formylation reaction, hydroaminomethylation reaction, transfer hydrogenation reaction, allylation reaction, olefin metathesis reaction, cycloisomerization reaction, Diels-Alder reaction, asymmetric coupling reaction, Aldol reaction, Michael addition reaction, asymmetric epoxidation reaction, kinetic resolution and [m+n] cyclization reaction.

The diphosphine ruthenium acetate complex prepared from the compound has a high activity and an enantioselectivity of greater than 99% for the hydrogenation of unsaturated carboxylic acids in organic solvents.

The diphosphine ruthenium acetate complex is a compound having a structure below:

Structure: diphosphine ruthenium acetate complex with Ph₂ groups and R substituents R = alkyl, fluoroalkyl or aryl where R=alkyl, fluoroalkyl or aryl; and alkyl and aryl as defined above are preferred.

Specifically, in a preferred catalytic asymmetric reaction, the compound is used as a catalyst, and the reaction route is as follows:

$$\underset{COOH}{\overset{R^1 \quad R^2}{\diagdown / }} \xrightarrow[\text{MeOH, rt}]{\text{Cat, H}_2 \text{ (10 atm)}} \underset{COOH}{\overset{R^1 \quad R^2}{\diagdown / }}$$

up to >99 ee

Cat = diphosphine ruthenium acetate complex structure

R = alkyl, fluoroalkyl or aryl where R=alkyl, fluoroalkyl or aryl; and preferably alkyl and aryl as defined above.

Another object of the present invention is to provide a bisphosphine ruthenium acetate complex, which has high activity and enantioselectivity for hydrogenation of unsaturated carboxylic acids in an organic solvent. The bisphosphine ruthenium acetate complex is a compound shown below:

Structure: bisphosphine ruthenium acetate complex

R = alkyl, fluoroalkyl or aryl where R=alkyl, fluoroalkyl or aryl; and alkyl or aryl as defined above are preferred.

Compared with the prior art, the present application has the following beneficial effects.

(1) The oxa-spiro compound has central chirality, and thus include L-oxa-spirodiphosphine ligand and R-oxa-spirodiphosphine ligand. The racemic spirodiphosphine ligand can be synthesized from racemic oxa-spirobisphenol as a raw material.

(2) The present invention can be used as a chiral ligand in the asymmetric hydrogenation of unsaturated carboxylic acids. Its complex with ruthenium can achieve an enantioselectivity of greater than 99% in the asymmetric hydrogenation of methyl-cinnamic acid.

BRIEF DESCRIPTION OF THE DRAWINGS

FIG. 1 is a schematic view showing the preparation of various chiral compounds according to the present invention, and the corresponding conversion rates and enantioselectivity ee.

DESCRIPTION OF THE EMBODIMENTS

The present invention will be described below by way of examples with reference to accompanying drawings. However, the present invention is not limited thereto.

EXAMPLE 1

Synthesis of (R)-2-H,2'-H-3,3'-spirobi[benzofuran]-4,4'-di(trifluoromethanesulfonate) 2

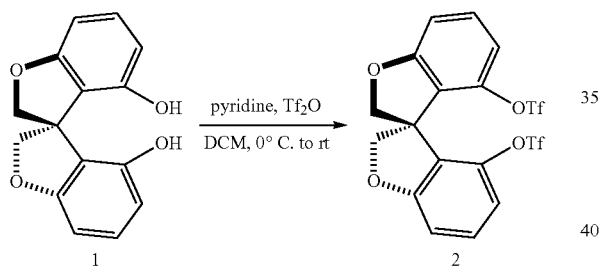

Under a $N_2$ atmosphere, (S)-6 (7.68 g, 30 mmol) was added to a 250 mL reaction flask, and then dry dichloromethane (150 mL) was added. Pyridine (6.0 mL, 100 mmol) was added with stirring at room temperature. After the reaction system became clear, it was cooled to 0° C., and then $Tf_2O$ (12.0 mL, 70 mmol) was added dropwise. After that, the reaction system was warmed to room temperature and continuously stirred for 1 h. The reaction was quenched with water. The reaction system was washed with dilute hydrochloric acid, and the organic phase was removed of the solvent under reduced pressure, and then purified by column chromatography to obtain the product (S)-7 (15.6 g, yield: 99%)

White solid. $^1$H NMR (500 MHz, CDCl$_3$) δ 4.70 (d, J=10.0 Hz, 2H, CH$_2$), 4.87-4.90 (m, 2H, CH$_2$), 6.91-6.93 (m, 4H, Ar), 7.32 (dd, J$_1$=8.5 Hz, J$_2$=8.0 Hz, 2H, Ar). $^{13}$C {1H} NMR (126 MHz, CDCl$_3$) δ 162.3, 145.8, 131.9, 119.8, 118.1 (q, J=320.0 Hz, CF$_3$), 113.1, 110.4, 82.5, 54.9. $^{19}$C {1H} NMR (126 MHz, CDCl$_3$) δ −74.23. HRMS (EST) calcd. for C$_{17}$H$_1$F$_6$O$_8$S$_2$ [M+H]$^+$: 520.9800, Found: 520.9794, [α]$^{20}_D$=+19.2 (c=0.5, acetone).

EXAMPLE 2

Synthesis of (R)-4'-(diphenylphosphine oxide)-2H,2'H-3,3'-spirobi[benzofuran]-4-trifluoromethanesulfonate 3a

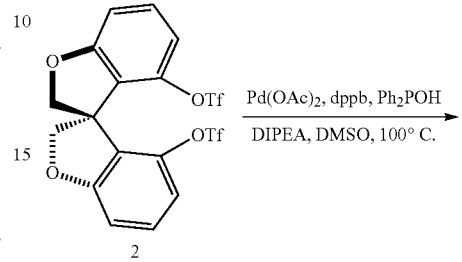

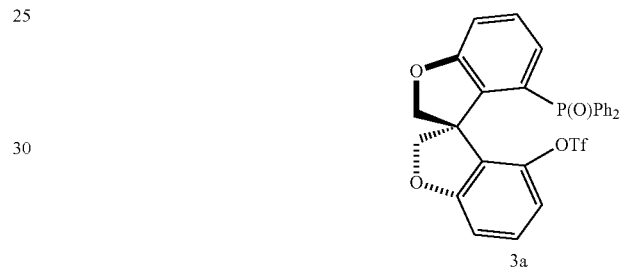

Under a $N_2$ atmosphere, 2 (5.2 g, 10 mmol), dppb (213 mg, 0.05 mmol), Ph$_2$POH (3.87 g, 15 mmol), Pd(OAc)$_2$ (112 mg, 0.05 mmol), and DIPEA (6.5 mL, 40 mmol) were added to a reaction flask, and finally DMSO (50 mL) containing no water and oxygen was added. The reaction was continued at 100° C. for 6 h. After cooling to room temperature, water was added to quench the reaction, and the reaction system was extracted with ethyl acetate. The organic phase was dried over anhydrous sodium sulfate, removed of the solvent under reduced pressure, and simply purified by column chromatography to obtain the product 3a (5.15 g, yield=90%).

White solid. $^1$H NMR (400 MHz, CDCl$_3$) δ 4.64-4.68 (m, 2H, CH$_2$), 4.77 (d, J=9.6 Hz, 1H, CH$_2$), 5.15-5.18 (m, 1H, CH$_2$), 6.40 (d, J=8.0 Hz, 1H, Ar), 6.58-6.60 (m, 1H, Ar), 6.78-6.80 (m, 1H, Ar), 6.88-6.90 (m, 1H, Ar), 6.94-6.98 (m, 2H, Ar), 7.05-7.13 (m, 3H, Ar), 7.16-7.20 (m, 2H, Ar), 7.24-7.28 (m, 4H, Ar). $^{13}$C {1H} NMR (101 MHz, CDCl$_3$) δ 162.6, 160.3, 145.4, 136.6, 134.5, 133.4 (m), 132.3, 132.0, 131.2, 130.0, 128.4 (m), 122.6 (m), 120.7, 112.3, 110.9, 109.4, 84.5, 82.9, 56.3, 26.9. $^{31}$P {1H} NMR (202 MHz, CDCl$_3$) δ 21.95 (s). HRMS (ESI) calcd. for C$_{18}$H$_{21}$O$_6$F$_3$PS [M+H]$^+$: 573.0749, Found: 573.0743, [α]$^{20}_D$=+237.2 (c=0.5, acetone).

EXAMPLE 3

Synthesis of (R)-4'-(diphenylphosphine)-2H,2'H-3,3'-spirobi[benzofuran]-4-trifluoromethanesulfonate 4a

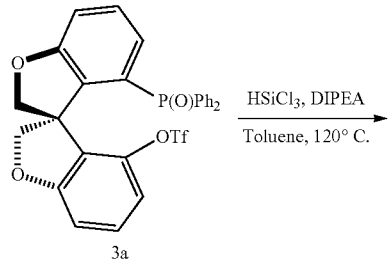

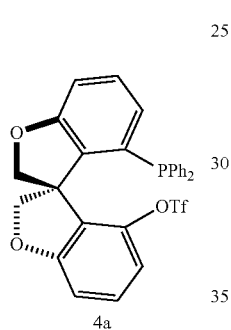

In a 100 mL sealed tube, 3a (2.86 g, 5 mmol), DIPEA (6.6 mL, 40 mmol), 20 mL toluene, and trichlorosilane (2.0 mL, 20 mmol) were added. The reaction was stirred overnight at 120° C. The reaction system was quenched with excess saturated sodium bicarbonate solution, added with ethyl acetate (100 mL), and filtered through celite, and the organic phase was dried over anhydrous sodium sulfate. The organic phase was then removed of the solvent under reduced pressure, and then purified by column chromatography to obtain 4a as a white solid (2.5 g, yield=90%).

White solid. $^1$H NMR (400 MHz, CDCl$_3$) δ 4.58-4.62 (m, 2H, CH$_2$), 4.69-4.72 (m, 1H, CH$_2$), 5.08-5.12 (m, 1H, CH$_2$), 6.32-6.34 (m, 1H, Ar), 6.51-6.52 (m, 1H, Ar), 6.72-6.74 (m, 1H, Ar), 6.81-6.85 (m, 1H, Ar), 6.88-6.91 (m, 2H, Ar), 6.99-7.05 (m, 3H, Ar), 7.10-7.13 (m, 2H, Ar), 7.14-7.22 (m, 4H, Ar). $^{13}$C {1H} NMR (126 MHz, CDCl$_3$) δ 162.6, 160.3, 145.4, 136.6, 134.5 (m), 133.5 (m), 132.0, 131.3, 130.1, 128.8 (m), 127.8, 122.6, 112.3, 110.9, 109.5, 84.5, 83.0, 56.3. $^{31}$P {1H} NMR (202 MHz, CDCl$_3$) δ −22.32. (s). HRMS (ESI) calcd. for C$_{18}$H$_{21}$O$_5$F$_3$PS [M+H]$^+$: 557.0799, Found: 557.0794, [α]$^{20}$$_D$=α56.0 (c=0.5, acetone).

EXAMPLE 4

Synthesis of (R)-(4'-(diphenylphosphine)-2H,2'H-3,3'-spirobi[benzofuran]-4-diphenylphosphine oxide 5a

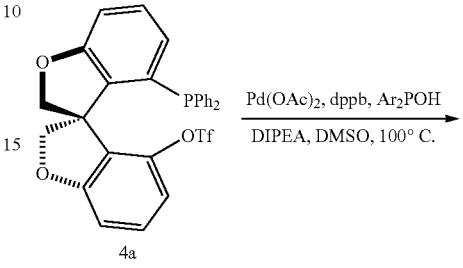

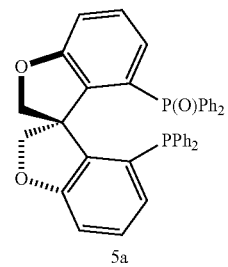

Under a N$_2$ atmosphere, 4a (2.78 g, 5 mmol), dppb (107 mg, 0.025 mmol), Ph$_2$POH (1.94 g, 7.5 mmol), Pd(OAc)$_2$ (56 mg, 0.0025 mmol), and DIPEA (3.2 mL, 20 mmol) were added to a reaction flask, and finally DMSO (20 mL) containing no water and oxygen was added. The reaction was continued at 100° C. for 6 h. After cooling to room temperature, water was added to quench the reaction, and the reaction system was extracted with ethyl acetate. The organic phase was dried over anhydrous sodium sulfate, removed of the solvent under reduced pressure, and simply purified by column chromatography to obtain the product 5a (2.66 g, yield=87%).

White solid. $^1$H NMR (500 MHz, CDCl$_3$) δ 4.38 (d, J=9.5 Hz, 1H, CH$_2$), 4.43 (d, J=9.0 Hz, 1H, CH$_2$), 4.46 (d, J=9.5 Hz, 1H, CH$_2$), 5.19 (d, J=9.0 Hz, 1H, CH$_2$), 6.56-6.59 (m, 1H, Ar), 6.74-6.84 (m, 4H, Ar), 7.01-7.03 (m, 1H, Ar), 7.07-7.12 (m, 3H, Ar), 7.17-7.30 (m, 6H, Ar), 7.32-7.36 (m, 5H, Ar). 7.38-7.43 (m, 3H, Ar), 7.48-7.55 (m, 3H, Ar), $^{13}$C {1H} NIMR (126 MHz, CDCl$_3$) δ 162.9, 160.4, 138.1, 137.9, 137.4, 134.9, 134.4 (m), 134.1 (m), 133.3 (m), 132.5, 132.1, 131.7 (m), 129.8, 128.9 (m), 128.4 (m), 128.1 (m), 126.7 (m), 113.4, 110.2, 85.2, 84.0, 58.2 (m). $^{31}$P {1H} NMR (162 MHz, CDCl$_3$) δ 29.41 (s), −20.96 (s). HRMS (ESI) calcd. for C$_{39}$H$_{31}$O$_3$P$_2$ [M+H]$^+$: 609.1748, Found: 609.1743, [α]$^{20}$$_D$=+224.0 (c=0.5, acetone).

EXAMPLE 5

Synthesis of (R)-4,4'-bis(dinhenylphosphine)-2H, 2'H-3,3'-spirobi[benzofuran] 6a

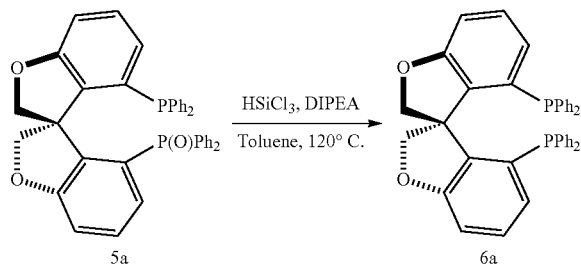

In a 100 mL sealed tube, 3a (1.216 g, 2 mmol), DIPEA (3.3 mL, 20 mmol), toluene (10 mL), and trichlorosilane (1.0 mL, 10 mmol) were added. The reaction was stirred overnight at 120° C. The reaction system was quenched with excess saturated sodium bicarbonate solution, added with ethyl acetate (100 mL), and filtered through celite, and the organic phase was dried over anhydrous sodium sulfate. The organic phase was then removed of the solvent under reduced pressure, and then purified by column chromatography to obtain 6a as a white solid (1.15 g, yield=96%).

White solid. $^1$H NMR (500 MHz, CDCl$_3$) δ 4.38 (d, J=9.5 Hz, 2H, CH$_2$), 4.49 (d, J=9.5 Hz, 2H, CH$_2$), 6.67-6.68 (m, 2H, Ar), 6.85-6.86 (m, 2H, Ar), 6.92 (s, 4H, Ar), 7.01-7.03 (m, 1H, Ar), 7.11-7.23 (m, 12H, Ar), 7.29-7.30 (m, 6H, Ar), $^{13}$C {1H} NMR (126 MHz, CDCl$_3$) δ 160.8 (t, J=7.5 Hz), 137.1, 136.8, 135.0, 134.1, 133.4, 129.5, 128.7 128.4, 128.0, 127.3, 110.4, 83.6, 58.0 (m). $^{31}$P {1H} NMR (162 MHz, CDCl$_3$) δ −20.99 (s). HRMS (ESI) calcd. for C$_{39}$H$_{31}$O$_2$P$_2$ [M+H]$^+$: 593.1799, Found: 593.1782, [α]$^{20}_D$=+246 (c=0.5, acetone).

EXAMPLE 6

Synthesis of (R)-4'-(di-p-methylphenylphosphine oxide)-2H,2'H-3,3'-spirobi[benzofuran]-4-trifluoromethanesulfonate 3b

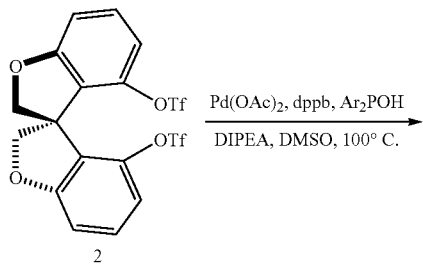

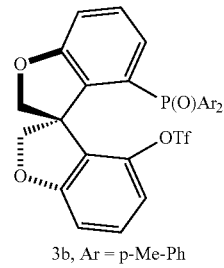

3b, Ar = p-Me-Ph

Under a N$_2$ atmosphere, 2 (2.6 g, 5 mmol), dppb (107 mg, 0.025 mmol), Ar$_2$POH (1.73 g, 7.5 mmol), Pd(OAc)$_2$ (56 mg, 0.025 mmol), and DIPEA, (3.2 mL, 20 mmol) were added to a reaction flask, and finally DMSO (30 mL) containing no water and oxygen was added. The reaction was continued at 100° C. for 6 h. After cooling to room temperature, water was added to quench the reaction, and the reaction system was extracted with ethyl acetate. The organic phase was dried over anhydrous sodium sulfate, removed of the solvent under reduced pressure, and simply purified by column chromatography to obtain the product 3b (2.60 g, yield=87%).

White solid. $^1$H NMR (500 MHz, CDCl$_3$) δ 2.36 (s, 3H, CH$_3$), 2.38 (s, 3H, CH$_3$), 4.60-4.62 (m, 1H, CH$_2$), 4.70-4.74 (m, 2H, CH$_2$), 5.69 (d, J=8.5 Hz, 1H, CH$_2$), 6.17 (d, J=8.0 Hz, 1H, Ar), 6.66-6.70 (m, 1H, Ar), 6.80-6.81 (m, 1H, Ar), 7.03-7.07 (m, 2H, Ar), 7.10-7.16 (m, 4H, Ar), 7.18-7.21 (m, 3H, Ar), 7.36-7.40 (m, 2H, Ar). $^{13}$C {1H} NMR (126 MHz, CDCl$_3$) δ 163.8, 161.9, 144.7, 142.0 (m), 131.9 (m), 131.5 (m), 131.2 (m), 130.7 (m), 130.2, 130.0, 129.3, 129.0 (m), 128.1, 126.9, 123.5, 121.8, 119.8, 116.6, 113.8, 111.7, 109.3, 85.6, 83.6, 56.5, 21.5. $^{31}$P {1H} NMR (202 MHz, CDCl$_3$) δ 29.86 (s). HRMS (ESI) calcd. for C$_{30}$H$_{25}$O$_6$F$_3$PS [M+H]$^+$: 601.1062, Found: 601.1056, [α]$^{20}_D$=+108.4 (c=0.5, acetone).

EXAMPLE 7

Synthesis of (R)-4'-(di-p-methylphenylphosphine)-2H-2'H-3,3'-spirobi[benzofuran]-4-trifluorornethanesulfonate 4b

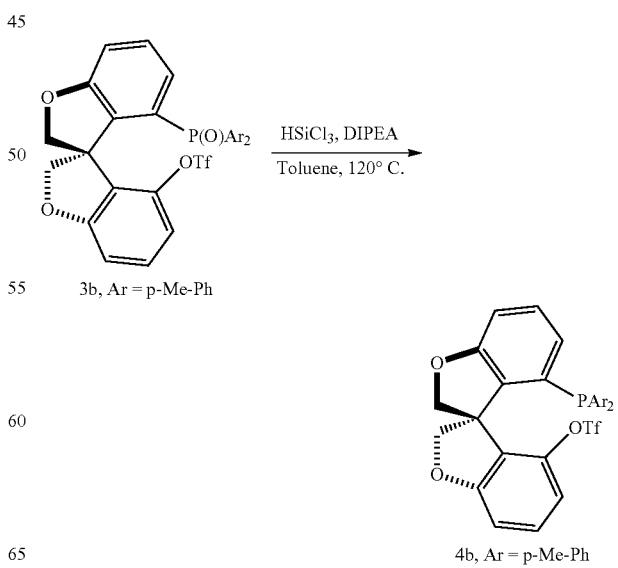

3b, Ar = p-Me-Ph

4b, Ar = p-Me-Ph

In a 100 mL sealed tube, 3b (3.00 g, 5 mmol), DIPEA (3.2 mL, 20 mmol), toluene (20 mL), and trichlorosilane (2.0 mL, 20 mmol) were added. The reaction was stirred overnight at 120° C. The reaction system was quenched with excess saturated sodium bicarbonate solution, added with ethyl acetate (100 mL), and filtered through celite, and the organic phase was dried over anhydrous sodium sulfate. The organic phase was then removed of the solvent under reduced pressure, and then purified by column chromatography to obtain 4b as a white solid (2.70 g, yield=92%).

White solid. $^1$H NMR (400 MHz, CDCl$_3$) δ 4.58-4.62 (m, 2H, CH$_2$), 4.69-4.72 (m, 1H, CH$_2$), 5.08-5.12 (m, 1H, CH$_2$), 6.43 (d, J=9.0 Hz, 1H, Ar), 6.51-6.52 (m, 1H, Ar), 6.72-6.74 (m, 1H, Ar), 6.81-6.85 (m, 1H, Ar), 6.88-6.91 (m, 2H, Ar), 6.99-7.05 (m, 3H, Ar), 7.10-7.13 (m, 2H, Ar), 7.14-7.22 (m, 4H, Ar). $^{13}$C {1H} NMR (101 MHz, CDCl$_3$) δ 162.7, 160.2, 153.6, 145.5, 138.6, 133.7, 133.5, 131.1, 129.9, 129.3, 129.0, 127.6, 122.6, 112.3, 110.7, 109.4, 84.3, 82.9, 56.3, 26.9, 21.2. $^{31}$P {1H} NMR (202 MHz, CDCl$_3$) δ−22.32 (s). HRMS (EST) calcd. for C$_{30}$H$_{25}$O$_5$F$_3$PS [M+H]$^+$: 585.1112, Found: 585.1107, [α]$^{20}_D$=+111.4 (c=0.5, acetone).

EXAMPLE 8

Synthesis of (R)-(4'-(di-p-methylphenylphosphine)-2H,2'H-3,3'-spirobi[benzofuran]-4-diphenylphosphine oxide 5b Under a N$_2$ atmosphere, 4b (0.584 g, 2 mmol), dppb (43 mg, 0.1 mmol), Ph$_2$POH (0.69 g, 3 mmol), Pd(OAc)$_2$ (22.4 mg, 0.1 mmol), and DIPEA (0.50 mL, 4 mmol) were added to a reaction flask, and finally DMSO (20 mL) containing no water and oxygen was added. The reaction was continued at 100° C. for 6 h. After cooling to room temperature, water was added to quench the reaction, and the reaction system was extracted with ethyl acetate. The organic phase was dried over anhydrous sodium sulfate, removed of the solvent under reduced pressure, and simply purified by column chromatography to obtain the product 5b (1.12 g, yield=85%).

White solid. $^1$H NMR (500 MHz, CDCl$_3$) δ 2.27 (s, 3H, CH$_3$), 2.31 (s, 6H, CH$_3$), 2.35 (s, 3H, CH$_3$) 4.36 (d, J=9.0 Hz, 1H, CH$_2$), 4.44 (t, J=9.5 Hz, 2H, CH$_2$), 5.25 (d, J=9.0 Hz, 1H, CH$_2$), 6.56-6.58 (m, 1H, Ar), 6.67-6.70 (m, 2H, Ar), 6.74-6.78 (m, 1H, Ar), 6.79-6.80 (m, 1H, Ar), 6.89-6.91 (m, 2H, Ar), 6.97-7.00 (m, 3H, Ar), 7.04-7.12 (m, 5H, Ar), 7.18-7.26 (m, 5H, Ar), 7.37-7.42 (m, 2H, Ar). $^{13}$C {1H} NMR (126 MHz, CDCl$_3$) δ 171.0, 162.8, 160.2, 141.7, 141.5, 138.5, 137.8, 137.6, 137.3, 134.0 (m), 133.2, 132.1, 131.7, 131.2, 130.0, 129.2 (m), 128.7 (m), 126.4, 113.0, 109.9, 85.0, 84.0, 60.3, 58.1 (m), 21.5, 21.2. $^{31}$P {1H} NMR (202 MHz, CDCl$_3$) δ 29.37 (s), −22.71 (s). HRMS (ESI) calcd. for C$_{43}$H$_{39}$O$_3$P$_2$ [M+H]$^+$: 665.2374, Found: 665.2369, [α]$^{20}_D$=+211.2 (c=0.5, acetone).

EXAMPLE 9

Synthesis of (R)-4,4'-bis(di-p-methylphenylphosphine)-2H,2'H-3,3'-spirobi[benzafuran] 6b

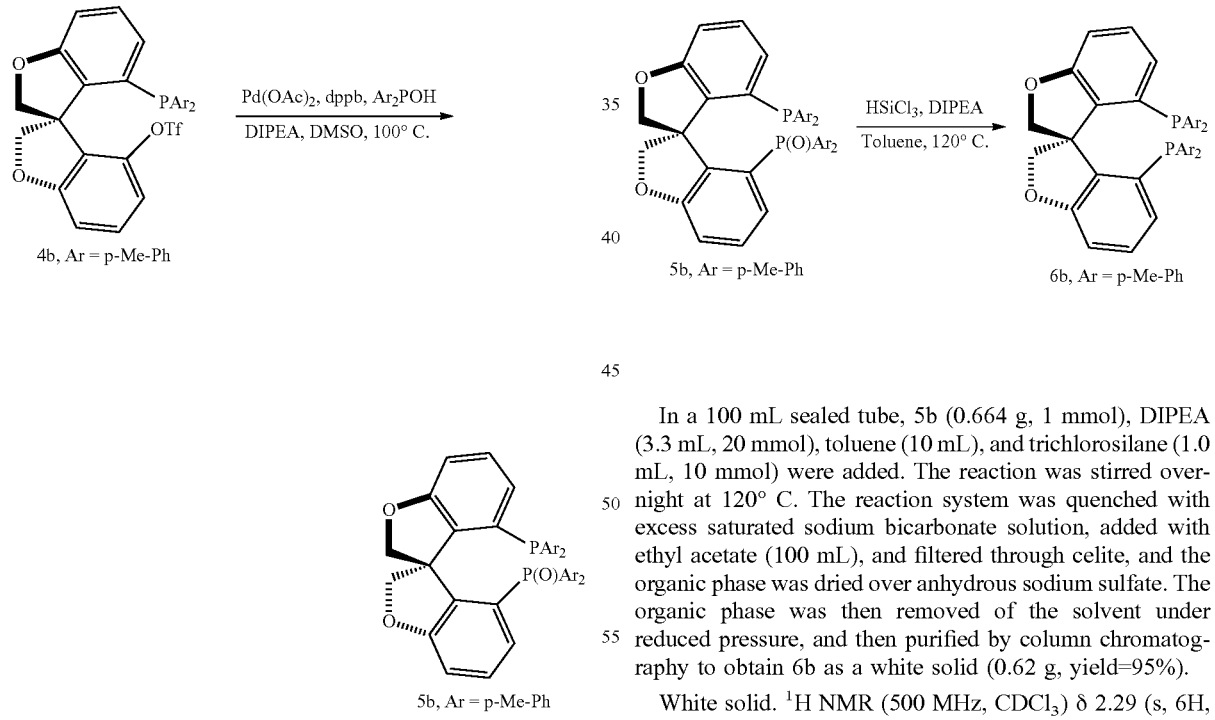

In a 100 mL sealed tube, 5b (0.664 g, 1 mmol), DIPEA (3.3 mL, 20 mmol), toluene (10 mL), and trichlorosilane (1.0 mL, 10 mmol) were added. The reaction was stirred overnight at 120° C. The reaction system was quenched with excess saturated sodium bicarbonate solution, added with ethyl acetate (100 mL), and filtered through celite, and the organic phase was dried over anhydrous sodium sulfate. The organic phase was then removed of the solvent under reduced pressure, and then purified by column chromatography to obtain 6b as a white solid (0.62 g, yield=95%).

White solid. $^1$H NMR (500 MHz, CDCl$_3$) δ 2.29 (s, 6H, CH$_3$), 2.33 (s, 6H, CH$_3$), 4.35 (d, J=9.5 Hz, 2H, CH$_2$), 4.44 (d, J=9.0 Hz, 2H, CH$_2$), 6.66-6.68 (m, 2H, Ar), 6.81-6.84 (m, 6H, Ar), 6.93-6.95 (m, 4H, Ar), 7.10 (s, 8H, Ar), 7.14-7.17 (m, 2H, Ar). $^{13}$C {1H} NMR (126 MHz, CDCl$_3$) δ 160.8 (m), 138.6, 137.7, 135.8, 134.8 (m), 134.2 (m), 133.5 (m), 129.2 (m), 128.8 (m), 110.1, 83.6 (m), 58.0 (m), 21.3. $^{31}$P {1H} NMR (202 MHz, CDCl$_3$) δ −22.82 (s). HRMS (ESI) calcd. for C$_{43}$H$_{39}$O$_2$P$_2$ [M+H]$^+$: 649.2425, Found: 649.2420, [α]$^{20}_D$=+231.2 (c=0.5, acetone).

EXAMPLE 10

Synthesis of (R)-4'-(di-p-methoxyphenylphosphine oxide)-2H,2'H-3,3'-spirobi[benzofuran]-4-trifluoromethanesulfonate 3c

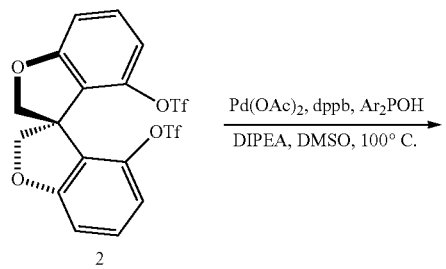

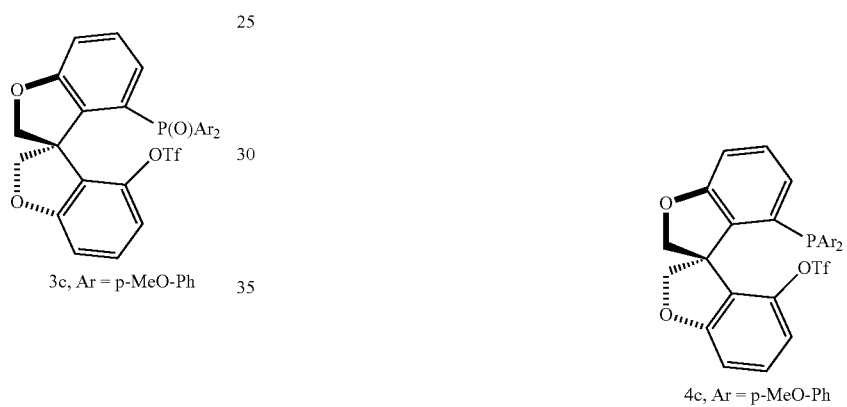

3c, Ar = p-MeO-Ph

Under a $N_2$ atmosphere, 2 (5.2 g, 10 mmol), dppb (213 mg, 0.05 mmol), $Ar_2POH$ (3.93 g, 15 mmol), $Pd(OAc)_2$ (112 mg, 0.05 mmol), and DIPEA (6.5 mL, 40 mmol) were added to a reaction flask, and finally DMSO (50 mL) containing no water and oxygen was added. The reaction was continued at 100° C. for 6 h. After cooling to room temperature, water was added to quench the reaction, and the reaction system was extracted with ethyl acetate. The organic phase was dried over anhydrous sodium sulfate, removed of the solvent under reduced pressure, and simply purified by column chromatography to obtain the product 3c (5.78 g, yield=91%).

White solid. $^1$H NMR (500 MHz, $CDCl_3$) δ 3.81 (s, 3H, $CH_3$), 3.84 (s, 3H, $CH_3$), 4.62 (d, J=9.5 Hz, 1H, $CH_2$), 4.70-4.75 (m, 2H, $CH_2$), 5.71 (d, J=8.5 Hz, 1H, $CH_2$), 6.23 (d, J=8.5 Hz, 1H, $CH_2$), 6.65-6.70 (m, 1H, Ar), 6.80-6.82 (m, 3H, Ar), 6.88-6.91 (m, 2H, Ar), 7.03-7.07 (m, 2H, Ar), 7.16-7.27 (m, 3H, Ar), 7.39-7.43 (m, 2H, Ar). $^{13}$C {1H} NMR (126 MHz, $CDCl_3$) δ 163.8, 162.2 (m), 144.7, 133.7, 133.0, 131.4 (m), 130.3 (m), 129.3, 126.9, 125.9, 125.0, 122.8, 121.7 (m), 119.1, 116.6, 113.8 (m), 111.5, 109.2, 85.6, 83.6, 56.5, 55.2. $^{31}$P {1H} NMR (202 MHz, $CDCl_3$) δ 29.39 (s). HRMS (ESI) calcd. for $C_{30}H_{25}O_8F_3PS$ [M+H]$^+$: 633.0960, Found: 633.0954, $[α]^{20}_D$=+62.4 (c=0.5, acetone).

EXAMPLE 11

Synthesis of (R)-4'-(di-p-methoxyphenylphosphine)-2H,2'H-3,3'-spirobi[benzofuran]-4-trifluoromethanesulovate 4c

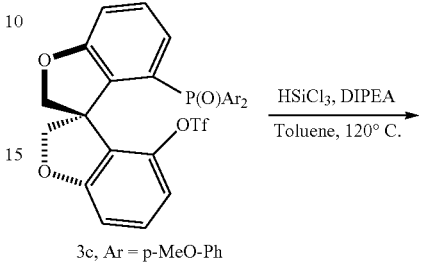

3c, Ar = p-MeO-Ph

4c, Ar = p-MeO-Ph

In a 100 mL sealed tube, 3c (2.86 g, 5 mmol), DIPEA (6.6 mL, 40 mmol), toluene (20 mL), and trichlorosilane (2.0 mL, 20 mmol) were added. The reaction was stirred overnight at 120° C. The reaction system was quenched with excess saturated sodium bicarbonate solution, added with ethyl acetate (100 mL), and filtered through celite, and the organic phase was dried over anhydrous sodium sulfate. The organic phase was then removed of the solvent under reduced pressure, and then purified by column chromatography to obtain 4c as a white solid (2.81 g, yield=91%).

White solid. $^1$H NMR (400 MHz, $CDCl_3$) δ 4.58-4.62 (m, 2H, $CH_2$), 4.69-4.72 (m, 1H, $CH_2$), 5.08-5.12 (m, 1H, $CH_2$), 6.43 (d, J=9.0 Hz, 1H, Ar), 6.51-6.52 (m, 1H, Ar), 6.72-6.74 (m, 1H, Ar), 6.81-6.85 (m, 1H, Ar), 6.88-6.91 (m, 2H, Ar), 6.99-7.05 (m, 3H, Ar), 7.10-7.13 (m, 2H, Ar), 7.14-7.22 (m, 4H, Ar). $^{13}$C NMR (101 MHz, $CDCl_3$) δ 162.7, 160.2, 153.6, 145.5, 138.6, 133.7, 133.5, 131.1, 129.9, 129.3, 129.0, 127.6, 122.6, 112.3, 110.7, 109.4, 84.3, 82.9, 56.3, 26.9, 21.2. $^{31}$P {1H} NMR (202 MHz, $CDCl_3$) δ −22.32 (s). HRMS (ESI) calcd. for $C_{30}H_{25}O_5F_3PS$ [M+H]$^+$: 585.1112, Found: 585.1107, $[α]^{20}_D$=+111.4 (c=0.5, acetone).

EXAMPLE 12

Synthesis of (R)-(4'-(di-p-methoxyphenylphosphine)-2H,2'H-3,3'-spirobi[benzofuran]-4-diphenylphosphine oxide 5c

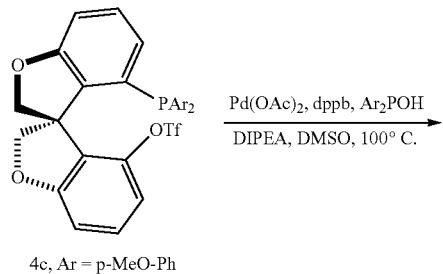

4c, Ar = p-MeO-Ph

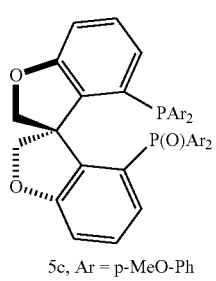

5c, Ar = p-MeO-Ph

Under a N$_2$ atmosphere, 4c (1.232 g, 2 mmol), dppb (43 mg, 0.1 mmol), Ph$_2$POH (0.79 g, 3 mmol), Pd(OAc)$_2$ (22.4 mg, 0.1 mmol), and DIPEA (1.6 mL, 5 mmol) were added to a reaction flask, and finally DMSO (20 mL) containing no water and oxygen was added. The reaction was continued at 100° C. for 6 h. After cooling to room temperature, water was added to quench the reaction, and the reaction system was extracted with ethyl acetate. The organic phase was dried over anhydrous sodium sulfate, removed of the solvent under reduced pressure, and simply purified by column chromatography to obtain the product 5c (1.27 g, yield=87%).

White solid. $^1$H NMR (500 MHz, CDCl$_3$) δ 3.73 (s, 3H, CH$_3$), 3.74 (s, 3H, CH$_3$), 3.77 (s, 6H, CH$_3$), 3.8 (s, 3H, CH$_3$) 4.37 (d, J=9.0 Hz, 1H, CH$_2$), 4.45-4.47 (m, 2H, CH$_2$), 5.28 (d, J=9.0 Hz, 1H, CH$_2$), 6.55-6.57 (m, 1H, Ar), 6.64-6.71 (m, 6H, Ar), 6.75-6.83 (m, 4H, Ar), 6.89-6.91 (m, 2H, Ar), 6.98-7.00 (m, 1H, Ar), 7.06-7.11 (m, 1H, Ar), 7.13-7.14 (m, 2H, Ar), 7.20-7.26 (m, 3H, Ar), 7.42-7.45 (m, 2H, Ar). $^{13}$C {1H} NMR (126 MHz, CDCl$_3$) δ 171.0, 162.8 (m), 161.9 (m), 160.3 (m), 137.5, 135.4, 134.8, 134.0 (m), 133.5, 130.6, 129.9, 128.5 (m), 128.1, 126.6 (m), 126.0 (m), 124.7, 123.8, 113.9 (m), 112.9, 109.8, 85.0, 84.2, 60.3, 58.1 (m), 55.0 (m). $^{31}$P {1H} NMR (202 MHz, CDCl$_3$) δ 28.75 (s), −24.27 (s). HERMS (ESI) calcd. for C$_{43}$H$_{39}$O$_7$P$_2$ [M+H]$^+$: 729.2171, Found: 729.2166, [α]$^{20}_D$=+173.2 (c=0.5, acetone).

EXAMPLE 13

Synthesis of (R)-4,4'-bis(di-p-methylphenylphosphine)-2H,2'H-3,3'-spirobi[benzofuran]6c

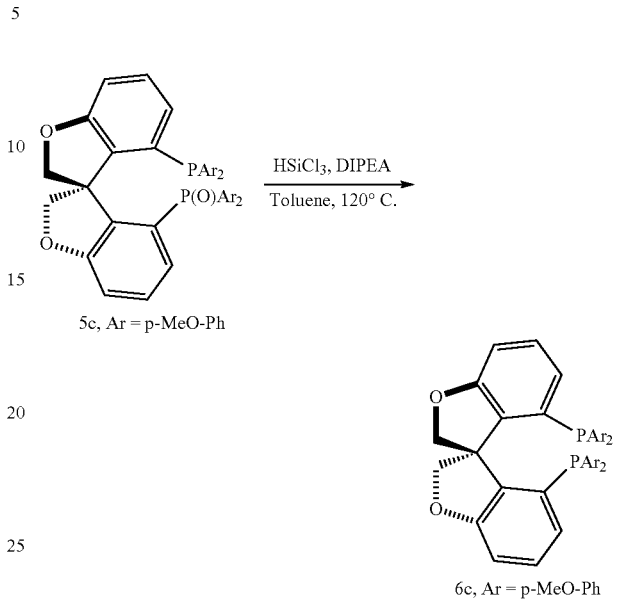

5c, Ar = p-MeO-Ph

6c, Ar = p-MeO-Ph

In a 100 mL sealed tube, 5c (0.728 g, 1 mmol), DIPEA (1.65 mL, 10 mmol), toluene (10 mL), and trichlorosilane (1.0 mL, 10 mmol) were added. The reaction was stirred overnight at 120° C. The reaction system was quenched with excess saturated sodium bicarbonate solution, added with ethyl acetate (100 mL), and filtered through celite, and the organic phase was dried over anhydrous sodium sulfate. The organic phase was then removed of the solvent under reduced pressure, and then purified by column chromatography to obtain 6c as a white solid (0.64 g, yield=90%).

White solid. $^1$H NMR (500 MHz, CDCl$_3$) δ 3.75 (s, 6H, CH$_3$), 3.79 (s, 6H, CH$_3$), 4.36 (d, J=9.0 Hz, 2H, CH$_2$), 4.46 (d, J=9.5 Hz, 2H, CH$_2$), 6.64-6.70 (m, 6H, Ar), 6.82-6.85 (m, 10H, Ar), 7.12-7.18 (m, 6H, Ar). $^{13}$C {1H} NMR (126 MHz, CDCl$_3$) δ 160.8 (m), 160.1 (m), 136.2 (m), 135.5 (m), 134.5 (m), 129.3, 128.3 (m), 126.8, 114.0 (m), 110.0, 83.6 (m), 57.9 (m), 55.1 (m). $^{31}$P {1H} NMR (202 MHz, CDCl$_3$) δ −24.20 (s). HRMS (ESI) calcd. for C$_{43}$H$_{39}$O$_2$P$_2$ [M+H]$^+$: 649.2425, Found: 649.2420, [α]$^{20}_D$=+133.6 (c=0.5, acetone).

EXAMPLE 14

Synthesis of (R)-4'-bis(3,5-dimethylphenyl)phosphine oxide)-2H,2'H-3,3'-spirobi[benzofuran]-4-trifluoromethanesulfonate 3d

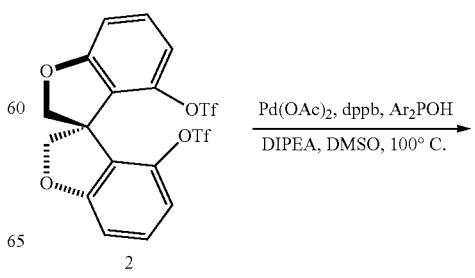

2

-continued

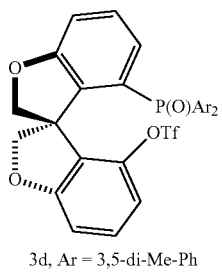

3d, Ar = 3,5-di-Me-Ph

Under a $N_2$ atmosphere, 2 (5.20 g, 10 mmol), dppb (213 mg, 0.05 mmol), $Ar_2POH$ (3.87 g, 15 mmol), $Pd(OAc)_2$ (112 mg, 0.05 mmol), and DIPEA (6.5 mL, 40 mmol) were added to a reaction flask, and finally DMSO (50 mL) containing no water and oxygen was added. The reaction was continued at 100° C. for 6 h. After cooling to room temperature, water was added to quench the reaction, and the reaction system was extracted with ethyl acetate. The organic phase was dried over anhydrous sodium sulfate, removed of the solvent under reduced pressure, and simply purified by column chromatography to obtain the product 3d (5.15 g, yield=82%).

White solid. $^1$H NMR (500 MHz, $CDCl_3$) δ 2.15 (s, 6H, $CH_3$), 2.17 (s, 6H, $CH_3$), 4.54 (d, J=9.5 Hz, 1H, $CH_2$), 4.62-464 (m, 2H, $CH_2$), 5.69 (d, J=8.5 Hz, 1H, $CH_3$), 6.07 (d, J=8.0 Hz, 1H, Ar), 6.63-6.67 (m, 1H, Ar), 6.72-6.78 (m, 3H, Ar), 6.93-6.98 (m, 2H, Ar), 7.00-7.05 (m, 4H, Ar), 7.12-7.18 (m, 1H, Ar). $^{13}$C {1H} NMR (126 MHz, $CDCl_3$) δ 163.9, 161.7, 144.7, 137.8 (m), 133.9, 133.3 (m), 131.5, 130.7, 130.0 (m), 129.4 (m), 128.7, 126.9, 121.6, 119.1, 116.5, 113.6, 111.3, 109.1, 85.7, 83.6, 56.3, 21.2. $^{31}$P {1H} NMR (202 MHz, $CDCl_3$) δ 29.59 (s). HRMS (ESI) calcd. for $C_{32}H_{29}O_6F_3PS$ [M+H]$^+$: 629.1375, Found: 629.1369, $[α]^{20}{}_D$=+196.4 (c=0.5, acetone).

EXAMPLE 15

Synthesis of (R)-4'-(3,5-dimethylphenylphosphine)-2H,2'H-3,3'-spirobi[benzofuran]-4-trifluoromethanesulfonate 4d

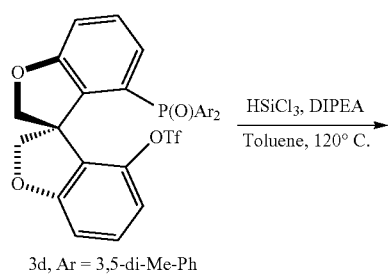

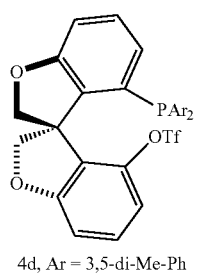

4d, Ar = 3,5-di-Me-Ph

In a 100 mL sealed tube, 3d (3.14 g, 5 mmol), DIPEA (6.6 mL, 40 mmol), (20 mL), and trichlorosilane (2.0 mL, 20 mmol) were added. The reaction was stirred overnight at 120° C. The reaction system was quenched with excess saturated sodium bicarbonate solution, added with ethyl acetate (100 mL), and filtered through celite, and the organic phase was dried over anhydrous sodium sulfate. The organic phase was then removed of the solvent under reduced pressure, and then purified by column chromatography to obtain 4d as a white solid (2.88 g, yield=94%).

White solid. $^1$H NMR (400 MHz, $CDCl_3$) δ 2.16 (s, 6H, $CH_3$), 2.19 (s, 6H, $CH_3$), 4.44 (d, J=9.0 Hz, 1H, $CH_2$), 4.63-4.67 (m, 2H, $CH_2$), 5.15-5.18 (m, 1H, $CH_2$), 6.36-6.40 (m, 1H, Ar), 6.51-6.53 (m, 3H, Ar), 6.65-6.68 (m, 1H, Ar), 6.73-6.79 (m, 3H, Ar), 6.83-6.87 (m, 3H, Ar), 6.99-7.01 (m, 1H, Ar), 7.11-7.15 (m, 1H, Ar). $^{13}$C {1H} NMR (101 MHz, $CDCl_3$) δ 162.6, 160.2, 145.3, 137.7 (m), 136.3, 135.2, 134.0, 131.8 (m), 130.5 (m), 129.9, 127.7, 122.8, 119.3, 116.7, 112.1, 110.6, 109.4, 84.4, 83.0, 56.2, 21.3. $^{31}$P {1H} NMR (162 MHz, $CDCl_3$) δ–21.56 (s). HRMS (ESI) calcd. for $C_{32}H_{29}O_5F_3PS$ [M+H]$^+$: 613.1425, Found: 613.1420, $[α]^{20}{}_C$=+60.0 (c=0.5, acetone).

EXAMPLE 16

Synthesis of (R)-(4'-(3,5-dimethylphenylphosphine)-2H,2'H-3,3'-spirobi[benzofuran]-4-diphenylphosphine oxide 5b

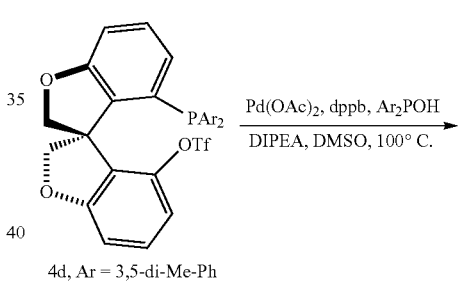

4d, Ar = 3,5-di-Me-Ph

5d, Ar = 3,5-di-Me-Ph

Under a $N_2$ atmosphere, 4d (1.22 g, 2 mmol), dppb (107 mg, 0.1 mmol), $Ph_2POH$ (0.77 g, 3 mmol), $Pd(OAc)_2$ (22.4 mg, 0.1 mmol), and DIPEA (0.8 mL, 5 mmol) were added to a reaction flask, and finally DMSO (10 mL) containing no water and oxygen was added. The reaction was continued at 100° C. for 6 h. After cooling to room temperature, water was added to quench the reaction, and the reaction system was extracted with ethyl acetate. The organic phase was dried over anhydrous sodium sulfate, removed of the solvent under reduced pressure, and simply purified by column chromatography to obtain the product 5d (1.22 g, yield=86%).

White solid. $^1$H NMR (500 MHz, $CDCl_3$) δ 2.04 (s, 6H, $CH_3$), 2.06 (s, 6H, $CH_3$), 2.24 (s, 6H, $CH_3$), 2.29 (s, 6H, CH$_3$), 4.14 (d, J=9.5 Hz, 1H, CH$_2$), 4.41 (d, J=9.5 Hz, 2H, CH$_2$), 5.15 (d, J=8.5 Hz, 1H, CH$_2$), 6.49 (d, J=7.5 Hz, 1H, Ar), 6.70-6.73 (m, 1H, Ar), 6.75-6.78 (m, 2H, Ar), 6.86-6.90 (m, 3H, Ar), 6.95-6.98 (m, 3H, Ar), 7.03-7.06 (m, 2H, Ar), 7.07 (s, 1H, Ar), 7.09 (s, 1H, Ar), 7.19 (s, 1H, Ar), 7.21 (s, 1H, Ar), 7.24-7.25 (m, 1H, Ar). $^{13}$C {1H} NMR (126 MHz, CDCl$_3$) δ 162.8 (m), 159.8 (m), 137.7 (m), 136.8 (m), 135.0, 134.2, 134.0, 133.2 (m), 132.8, 132.4 (m), 130.8 (m), 130.0 (m), 129.4 (m), 128.5 (m), 126.7, 126.4, 112.9, 109.9, 84.1, 83.3, 58.3 (m), 21.3 (m). $^{31}$P NMR (202 MHz, CDCl$_3$) δ −19.53 (s), 29.83 (s). HRMS (ESI) calcd. for C$_{47}$H$_{47}$O$_3$P$_2$ [M+H]$^+$: 721.3000, Found: 721.2995, [α]$^{20}_D$=+137.2 (c=0.5, acetone).

EXAMPLE 17

Synthesis of (R)-4,4'-bis(3,5-dimethylphenyl)phosphine-2H,2'H-3,3'-spirobi[benzofuran] 6d

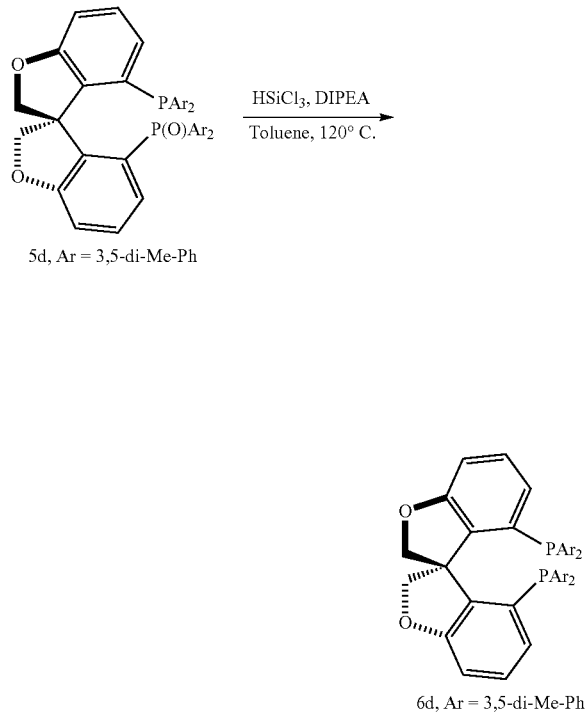

5d, Ar = 3,5-di-Me-Ph

6d, Ar = 3,5-di-Me-Ph

In a 100 mL sealed tube, 5d (0.72 g, 1 mmol), DIPEA (3.3 mL, 20 mmol), toluene (10 mL), and trichlorosilane (1.0 mL, 10 mmol) were added. The reaction was stirred overnight at 120° C. The reaction system was quenched with excess saturated sodium bicarbonate solution, added with ethyl acetate (100 mL), and filtered through celite, and the organic phase was dried over anhydrous sodium sulfate. The organic phase was then removed of the solvent under reduced pressure, and then purified by column chromatography to obtain 6d as a white solid (0.65 g, yield=93%).

White solid. $^1$H NMR (500 MHz, CDCl$_3$) δ 2.07 (s, 6H, CH$_3$), 2.09 (s, 6H, CH$_3$), 2.24 (s, 6H, CH$_3$), 2.26 (s, 6H, CH$_3$), 4.19-4.20 (m, 2H, CH$_2$), 4.31-4.34 (m, 2H, CH$_2$), 6.65-6.66 (m, 4H, Ar), 6.81-6.84 (m, 6H, Ar), 6.85-6.88 (m, 4H, Ar), 6.95-6.96 (m, 2H, Ar), 7.18-7.22 (m, 2H, Ar). $^{13}$C {1H} NMR (126 MHz, CDCl$_3$) δ 160.9 (m), 137.7 (m), 137.2 (m), 136.1, 133.8 (m), 132.3 (m), 131.0 (m), 129.6 (m), 127.1, 110.1, 82.9, 58.3 (m), 21.3 (m). $^{31}$P {1H} NMR (202 MHz, CDCl$_3$) δ −19.92 (s). HRMS (ESI) calcd. for C$_{47}$H$_{47}$O$_2$P$_2$ [M+H]$^+$: 705.3051, Found: 705.3046, [α]$^{20}_D$=+138.0 (c=0.5, acetone).

EXAMPLE 18

Synthesis of (R)-4'-(3,5-di-t-butylphenylphosphine oxide)-2H,2'H-3,3'-spirobi[benzofuran]-4-trifluoromethanesulfonate 3e

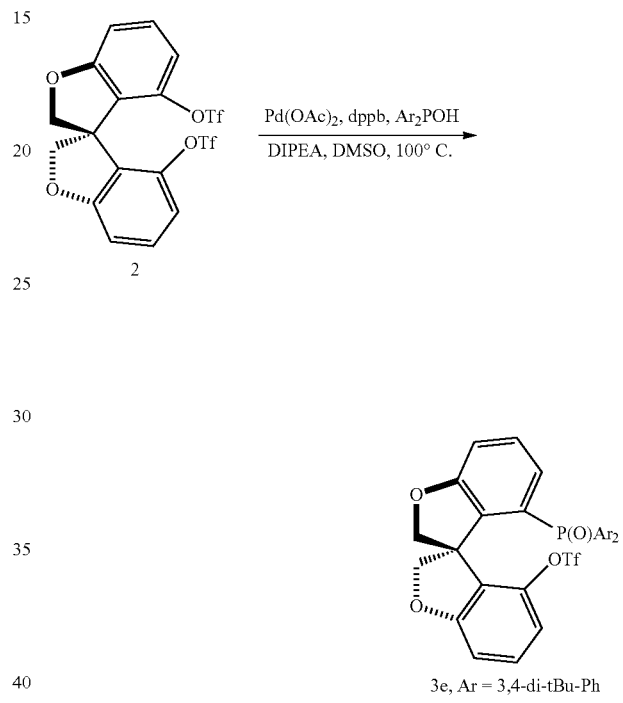

3e, Ar = 3,4-di-tBu-Ph

Under a N$_2$ atmosphere, 2 (5.2 g, 10 mmol), dppb (213 mg, 0.05 mmol), Ar$_2$POH (6.39 g, 15 mmol), Pd(OAc)$_2$ (112 mg, 0.05 mmol), and DIPEA (6.5 mL, 40 mmol) were added to a reaction flask, and finally DMSO (50 mL) containing no water and oxygen was added. The reaction was continued at 100° C. for 6 h. After cooling to room temperature, water was added to quench the reaction, and the reaction system was extracted with ethyl acetate. The organic phase was dried over anhydrous sodium sulfate, removed of the solvent under reduced pressure, and simply purified by column chromatography to obtain the product 3e (7.43 g, yield=93%), White solid. $^1$H NMR (500 MHz, CDCl$_3$) δ 1.18 (s, 9H, CH$_3$), 1.19 (s, 9H, CH$_3$), 1.20 (s, 9H, CH$_3$), 1.21 (s, 9H, CH$_3$), 4.54-4.56 (m, 1H, CH$_2$), 4.62-4.64 (m, 1H, CH$_2$), 4.80-482 (m, 2H, CH$_2$), 6.63-6.68 (m, 2H, Ar), 6.82-6.88 (m, 6H, Ar), 6.90-6.94 (m, 2H, Ar), 7.15-7.21 (m, 1H, Ar), 7.26-7.34 (m, 1H, Ar). $^{13}$C NMR (126 MHz, CDCl$_3$) δ 162.9, 160.1, 150.5, 150.2, 145.7, 136.0 (m), 135.5, 134.4, 131.2, 129.6, 128.4, 127.5, 122.4 (m), 112.5, 110.5, 109.6, 83.5, 82.3, 56.4 (m), 34.8 (m), 31.3 (m). $^{31}$P {1H} NMR (202 MHz, CDCl$_3$) δ −19.74 (s). HRMS (ESI) calcd. for C$_{44}$H$_{53}$O$_6$P$_3$PS [M+H]$^+$: 797.3253, Found: 797.3247, [α]$^{20}_D$=+109.6 (c=0.5, acetone).

EXAMPLE 19

Synthesis of (R)-4'-(3,5-di-t-butylphenylphosphine)-2H,2'H-3,3'-spirobi[benzofuran]-4-trifluoromethanesulfonate 4e

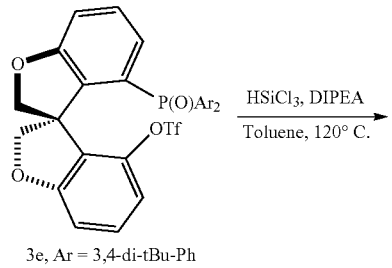

3e, Ar = 3,4-di-tBu-Ph

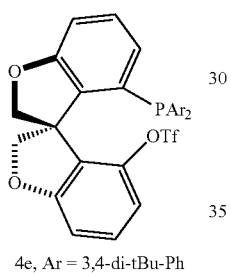

4e, Ar = 3,4-di-tBu-Ph

In a 100 mL sealed tube, 3e (3.98 g, 5 mmol), DIPEA (6.6 mL, 40 mmol), (20 mL), and trichlorosilane (2.0 mL, 20 mmol) were added. The reaction was stirred overnight at 120° C. The reaction system was quenched with excess saturated sodium bicarbonate solution, added with ethyl acetate (100 mL), and filtered through celite, and the organic phase was dried over anhydrous sodium sulfate. The organic phase was then removed of the solvent under reduced pressure, and then purified by column chromatography to obtain 4e as a white solid (3.51 g, yield=90%).

White solid. $^1$H NMR (500 MHz, CDCl$_3$) δ 1.17 (s, 9H, CH$_3$), 1.19 (s, 9H, CH$_3$), 1.20 (s, 9H, CH$_3$), 1.21 (s, 9H, CH$_3$), 4.52-4.55 (m, 1H, CH$_2$), 4.60-4.63 (m, 1H, CH$_2$), 4.77-4.82 (m, 2H, CH$_2$), 6.61-6.69 (m, 2H, Ar), 6.80-6.94 (m, 6H, Ar), 7.14-7.22 (m, 2H, Ar), 7.28-7.34 (m, 2H, Ar). $^{13}$C {1H} NMR (126 MHz, CDCl$_3$) δ 162.9, 160.1 (m), 150.5 (m), 145.8, 136.1 (m), 135.5 (m), 134.4, 131.9 (m), 131.2, 129.6, 128.4 (m), 127.5, 122.4 (m), 116.9, 112.6, 110.6, 109.6, 83.5, 82.4, 56.4 (m), 34.8 (m), 31.3 (m). $^{31}$P {1H} NMR (202 MHz, CDCl$_3$) δ −19.73 (s). HRMS (ESI) calcd. for C$_{32}$H$_{29}$O$_5$F$_3$PS [M+H]$^+$: 781.3303, Found: 781.3298, [α]$^{20}_D$=+78.8 (c=0.5, acetone).

EXAMPLE 20

Synthesis of (R)-(4'-(3,5-di-t-butylphenylphosphine)-2H,2'H-3,3'-spirobi[benzofuran]-4-diphenylphosphine oxide 5e

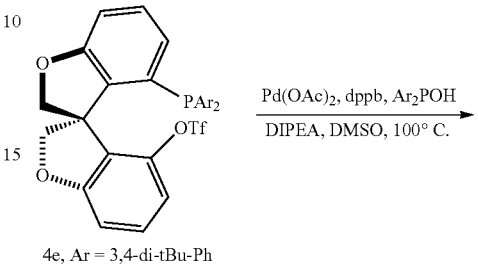

4e, Ar = 3,4-di-tBu-Ph

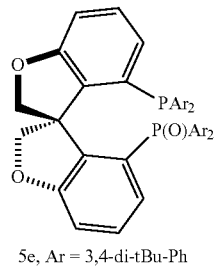

5e, Ar = 3,4-di-tBu-Ph

Under a N$_2$ atmosphere, 4e (1.56 g, 2 mmol), dppb (43 mg, 0.1 mmol), Ph$_2$POH (1.28 g, 3 mmol), Pd(OAc)$_2$ (22.4 mg, 0.1 mmol), and DIPEA (1.6 mL, 10 mmol) were added to a reaction flask, and finally DMSO (10 mL) containing no water and oxygen was added. The reaction was continued at 100° C. for 6 h. After cooling to room temperature, water was added to quench the reaction, and the reaction system was extracted with ethyl acetate. The organic phase was dried over anhydrous sodium sulfate, removed of the solvent under reduced pressure, and simply purified by column chromatography to obtain the product 5e (1.85 g, yield=92%).

White solid. $^1$H NMR (500 MHz, CDCl$_3$) δ 1.95 (s, 18H, CH$_3$), 1.02 (s. 18H, CH$_3$), 1.27 (s, 18H, CH$_3$), 1.30 (s, 18H, CH$_3$), 3.78 (d, J=8.8 Hz, 1H, CH$_2$), 4.36 (d, J=9.6 Hz, 1H, CH$_2$), 4.45 (d, J=8.4 Hz, 1H, CH$_2$), 4.91 (d, J=8.4 Hz, 1H, CH$_2$), 6.67 (d, J=6.8 Hz, 2H, Ar), 6.76-6.78 (m, 1H, Ar), 6.86-6.90 (m, 2H, Ar), 6.97-7.01 (m, 1H, Ar), 7.06-7.10 (m, 2H, Ar), 7.16-7.20 (m, 1H, Ar), 7.22-7.24 (m, 2H, Ar), 7.39 (s, 2H, Ar), 7.41 (s, 2H, Ar), 7.49 (s, 2H, Ar), 7.61 (d, J=8.0 Hz, 2H, Ar), 7.65 (d, J=9.6 Hz, 2H, Ar). $^{13}$C {1H} NMR (126 MHz, CDCl$_3$) δ 162.3, 159.0, 150.4 (m), 149.5 (m), 137.7, 137.3 (m), 135.5 (m), 134.7, 133.9 (m), 132.9, 132.4 (m), 129.6 (m). 128.0 (m), 127.5 (m), 126.5 (m). 122.9, 120.7, 112.2, 109.9, 81.4, 81.3, 59.1, 34.8 (m), 31.2 (m). $^{31}$P {1H} NMR (202 MHz, CDCl$_3$) δ 30.86 (s), −16.07 (s). HRMS (ESI) calcd. for C$_{71}$H$_{95}$O$_3$P$_2$ [M+H]$^+$: 1057.6756, Found: 1057.6751, [α]$^{20}_D$=+152.4 (c=0.5, acetone).

EXAMPLE 21

Synthesis of (R)-4,4'-bis(3,5-di-butylphenylphosphine)-2H,2'H-3,3'-spirobi[benzofuran] 6e

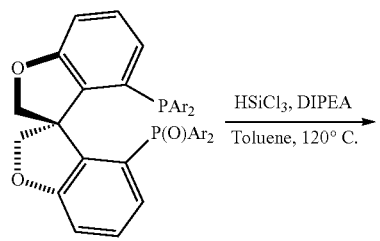

5e, Ar = 3,4-di-tBu-Ph

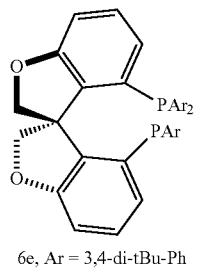

6e, Ar = 3,4-di-tBu-Ph

In a 100 mL sealed tube, 5e (1.01 g, 1 mmol), DIPEA (1.65 mL, 10 mmol), toluene (10 mL), and trichlorosilane (1.0 mL, 10 mmol) were added. The reaction was stirred overnight at 120° C. The reaction system was quenched with excess saturated sodium bicarbonate solution, added with ethyl acetate (100 mL), and filtered through celite, and the organic phase was dried over anhydrous sodium sulfate. The organic phase was then removed of the solvent under reduced pressure, and then purified by column chromatography to obtain 6e as a white solid (0.82 g, yield=79%).

White solid. $^1$H NMR (500 MHz, CDCl$_3$) δ 0.99 (s, 36H, CH$_3$), 1.25 (s, 36H, CH$_3$), 3.85 (d, J=9.0 Hz, 2H, CH$_2$), 4.25 (d, J=8.5 Hz, 2H, CH$_2$), 6.80 (d, J=8.0 Hz, 2H, Ar), 6.91-6.93 (m, 2H, Ar), 7.01-7.02 (m, 4H, Ar), 7.09-7.10 (m, 2H, Ar), 7.15-7.18 (m, 2H, Ar), 7.25-7.36 (m, 4H, Ar), 7.37 (s, 2H, Ar). $^{13}$C {1H} NMR (126 MHz, CDCl$_3$) δ 160.5 (m), 150.4 (m), 149.2 (m), 139.0, 137.4, 135.5 (m), 131.4 (m), 129.6 (m), 126.9 (m), 123.0, 120.9, 110.0, 80.4, 59.1 (m), 34.8 (m), 31.4 (m). $^{31}$P {1H} NMR (202 MHz, CDCl$_3$) δ −15.41 (s). HRMS (ESI) calcd. for C$_{71}$H$_{95}$O$_2$P$_2$ [M+H]$^+$: 1041.0807, Found: 1041.6802, $[\alpha]^{20}_D$=+140.4 (c=0.5, acetone).

EXAMPLE 22

Preparation of the Catalyst Ru(6a)OAc$_2$

Under a N$_2$ atmosphere, [RuPhCl$_2$]$_2$ (25 mg, 0.05 mmol) and the ligand 6a (61 mg, 0.103 mmol) were added to a 10 mL one-neck flask, and then DMF (2 mL) were added. The reaction was continued at 100° C. for 3 h. After cooling to room temperature, 1.5 mL of a solution of anhydrous sodium acetate (0.111 g, 1.3 mmol) in methanol was added. After 20 min, deoxygenated deionized water was added. A gray solid was precipitated from the reaction system, and filtered out. The solvent and water were removed under reduced pressure to obtain the catalyst Ru(6a)OAc$_2$ (57 mg, yield=71%).

EXAMPLE 23

Preparation of Catalyst Ru(6a)(CF$_3$CO)$_2$

Under a N$_2$ atmosphere, bis(2-methylallyl)-cycloocta-1,5-diene ruthenium (32 mg, 0.05 mmol) and the ligand 6a (61 mg, 0.103 mmol) were added to a 10 mL one-neck flask, and then acetone (2 mL) were added. The reaction was continued at 40° C. for 0.5 h. Then, trifluoroacetic acid (33 mg, 0.3 mmol) was added and stirred overnight at 40° C. The solvent was removed under reduced pressure, and then petroleum ether (1 mL) was added, and filtered to obtain the target product Ru(6a)(CF$_3$CO)$_2$ (81 mg, yield=88%).

EXAMPLE 24

Use of Ligand 6a in the Asymmetric Hydrogenation of 2-methylcinnamic acid

Under a N$_2$ atmosphere, 2-methylcinnamic acid (162 mg, 1 mmol), the catalyst Ru(6a)OAc$_2$ (0.8 mg, 0.001 mmol) and methanol (1 mL) were added to a hydrogenation vial. After 12 h under a hydrogen atmosphere of 10 atm, the raw material was completely converted into a product. The product and aniline were condensed to form an amide to measure the enantioselectivity of the product (ee>99%). HPLC conditions: Daicel ADH, volume of injection: 2 μL (c=1 mg/mL), IPA/hexane=90/10, 1.0 mL/Min, 210 nm, t$_R$ (major)=26.8 Min, t$_R$ (minor)=29.7 Min.

The conversion rate of various substances in the presence of 6a is shown in FIG. 1.

The foregoing is a further detailed description of the present invention in conjunction with specific preferred embodiments, and it should not be considered that the specific implementation of the present invention is limited thereto. Some simple deductions or replacements can be made by those ordinarily skilled in the art to which the present invention pertains without departing from the conception of the present invention, which are all regarded as falling within the protection scope of the present invention.

What is claimed is:

1. An oxa-spirodiphosphine ligand, having a structure of:

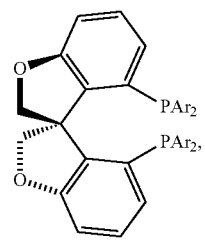

6b

Ar = p-Me—Ph

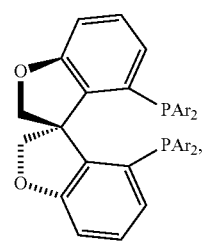

6c

Ar = p-MeO—Ph

-continued
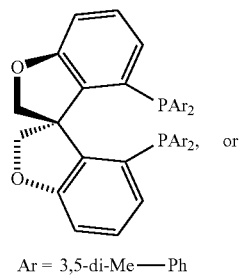
Ar = 3,5-di-Me—Ph
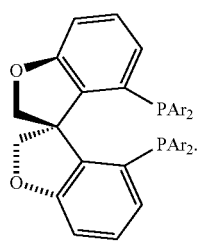
Ar = 3,4-di-tBu—Ph
2. A method for preparing the oxa-spirodiphosphine ligand according to claim 1, comprising:
step 1): preparing
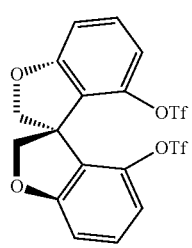
by adding Tf$_2$O into a first mixture containing
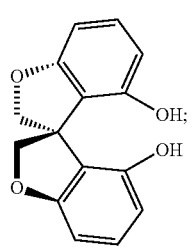
step 2): preparing
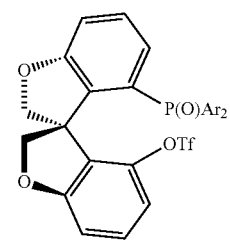
by adding Ar$_2$POH into a second mixture containing
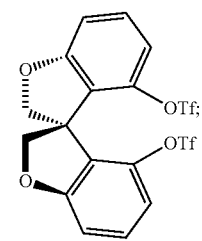
step 3): preparing
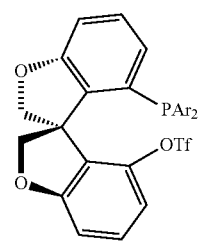
by adding trichlorosilane, DIPEA and toluene into
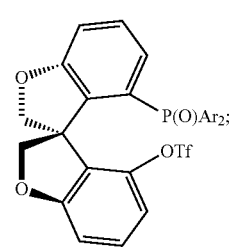

step 4): preparing

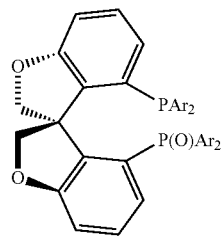

by adding Ar₂POH into a third mixture containing

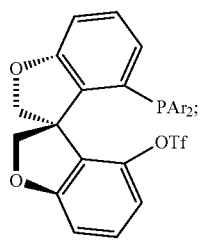

and
step 5): preparing

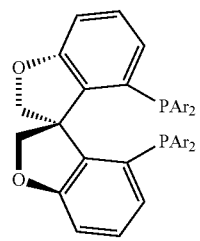

by adding trichlorosilane, DIPEA and toluene into

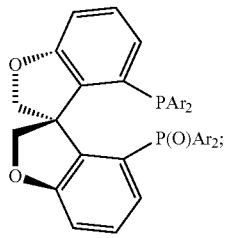

wherein Ar=p-Me-Ph, p-MeO-Ph, 3,5-di-Me-Ph or 3,4-di-tBu-Ph.

3. The method according to claim 2, wherein the first mixture further comprises pydine and dichloromethane.

4. The method according to claim 2, wherein both the second mixture and the third mixture comprise Pd(OAc)₂, dppb, DIPEA and DMSO.

5. A method for preparing diphosphine ruthenium acetate complex, comprising step of:
preparing the diphosphine ruthenium acetate complex by mixing the oxa-spirodiphosphine ligand according to claim 1 with a ruthenium containing compound, wherein the diphosphine ruthenium acetate complex has a structure of:

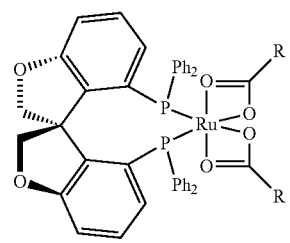

wherein R=alkyl; or

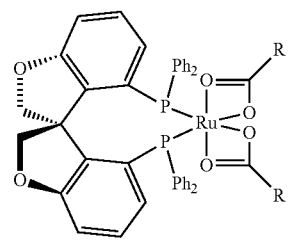

wherein R=fluoroalkyl; or

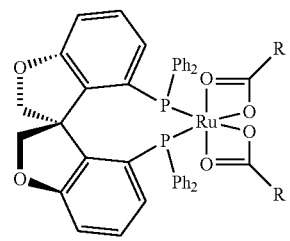

wherein R=aryl.

6. The method according to claim 5, wherein the diphosphine ruthenium acetate complex has a high activity and an enantioselectivity of greater than 99% for hydrogenation of unsaturated carboxylic acids in organic solvents.

* * * * *